(12) United States Patent
Yamano et al.

(10) Patent No.: US 11,088,391 B2
(45) Date of Patent: Aug. 10, 2021

(54) LITHIUM ION BATTERY

(71) Applicants: NATIONAL INSTITUTE OF ADVANCED INDUSTRIAL SCIENCE AND TECHNOLOGY, Tokyo (JP); MURATA MANUFACTURING CO., LTD., Kyoto (JP)

(72) Inventors: Akihiro Yamano, Osaka (JP); Tetsuo Sakai, Osaka (JP); Masahiro Yanagida, Osaka (JP); Masanori Morishita, Kyoto (JP); Masashi Higuchi, Kyoto (JP)

(73) Assignees: NATIONAL INSTITUTE OF ADVANCED INDUSTRIAL SCIENCE AND TECHNOLOGY, Tokyo (JP); MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 15/527,169

(22) PCT Filed: Oct. 19, 2015

(86) PCT No.: PCT/JP2015/079426
§ 371 (c)(1),
(2) Date: May 16, 2017

(87) PCT Pub. No.: WO2016/080128
PCT Pub. Date: May 26, 2016

(65) Prior Publication Data
US 2017/0338511 A1 Nov. 23, 2017

(30) Foreign Application Priority Data
Nov. 18, 2014 (JP) .............................. JP2014-233341

(51) Int. Cl.
*H01M 10/0525* (2010.01)
*H01M 4/133* (2010.01)
(Continued)

(52) U.S. Cl.
CPC ..... *H01M 10/0525* (2013.01); *H01M 4/0459* (2013.01); *H01M 4/131* (2013.01);
(Continued)

(58) Field of Classification Search
None
See application file for complete search history.

(56) References Cited

U.S. PATENT DOCUMENTS 5,340,672 A * 8/1994 Kubota ................... H01M 2/16
252/62.2
5,540,957 A * 7/1996 Ueda ........................ G11B 5/72
427/131

(Continued)

FOREIGN PATENT DOCUMENTS

JP 2003068358 A * 3/2003
JP 2003123740 A * 4/2003
(Continued)

OTHER PUBLICATIONS

JP2003-68358, Machine Translation, Isono (Year: 2003).*
(Continued)

*Primary Examiner* — Devina Pillay
(74) *Attorney, Agent, or Firm* — Nakanishi IP Associates, LLC

(57) ABSTRACT

Provided is a lithium ion battery whose manufacturing process is simple and which has high energy density and heat resistance. A lithium ion battery capable of storing and releasing lithium ions, and being provided with a separator between a positive electrode and a negative electrode having irreversible capacity at the initial charge/discharge, and (Continued)

having a structure in which void portions in the separator are filled with a nonaqueous electrolytic solution including lithium ions, wherein a positive electrode active material contained in the positive electrode has a first charge-discharge efficiency of 80% to 90% when charged/discharged using metal Li as an counter electrode; a negative electrode active material contained in the negative electrode includes a mixed material of a silicon compound and a carbon material; in the negative electrode, lithium corresponding to an irreversible capacity at the initial charge/discharge is not doped; a capacity ratio of the negative electrode to the positive electrode at the initial electric charge capacity of the positive electrode and the negative electrode is 0.95 or more and 1 or less; the positive electrode binder contained in the positive electrode is an aqueous binder; the negative electrode binder contained in the negative electrode is a polyimide; and the nonaqueous electrolyte contains lithium bis(oxalate) borate.

7 Claims, 2 Drawing Sheets

(51) Int. Cl.

| | | |
|---|---|---|
| *H01M 10/0569* | (2010.01) | |
| *H01M 4/525* | (2010.01) | |
| *H01M 4/131* | (2010.01) | |
| *H01M 10/0568* | (2010.01) | |
| *H01M 4/505* | (2010.01) | |
| *H01M 4/587* | (2010.01) | |
| *H01M 4/134* | (2010.01) | |
| *H01M 4/48* | (2010.01) | |
| *H01M 4/36* | (2006.01) | |
| *H01M 4/38* | (2006.01) | |
| *H01M 4/04* | (2006.01) | |
| *H01M 4/62* | (2006.01) | |
| *C08L 1/28* | (2006.01) | |
| *H01M 10/42* | (2006.01) | |
| *C08L 5/04* | (2006.01) | |
| *C01B 35/12* | (2006.01) | |
| *C07D 307/33* | (2006.01) | |
| *C08B 3/00* | (2006.01) | |
| *C08G 73/10* | (2006.01) | |
| *H01M 4/02* | (2006.01) | |

(52) U.S. Cl.
CPC ............ *H01M 4/133* (2013.01); *H01M 4/134* (2013.01); *H01M 4/364* (2013.01); *H01M 4/382* (2013.01); *H01M 4/386* (2013.01); *H01M 4/483* (2013.01); *H01M 4/505* (2013.01); *H01M 4/525* (2013.01); *H01M 4/587* (2013.01); *H01M 4/622* (2013.01); *H01M 10/0568* (2013.01); *H01M 10/0569* (2013.01); *C01B 35/12* (2013.01); *C07D 307/33* (2013.01); *C08B 3/00* (2013.01); *C08G 73/10* (2013.01); *C08L 1/286* (2013.01); *C08L 5/04* (2013.01); *H01M 4/621* (2013.01); *H01M 2004/027* (2013.01); *H01M 2004/028* (2013.01); *H01M 2010/4292* (2013.01); *H01M 2300/0028* (2013.01); *Y02P 70/50* (2015.11); *Y02T 10/70* (2013.01)

(56) References Cited

U.S. PATENT DOCUMENTS

| | | | |
|---|---|---|---|
| 2004/0023117 A1 | 2/2004 | Imachi et al. | |
| 2006/0099508 A1* | 5/2006 | Thackeray | ............ H01M 4/131 |
| | | | 429/231.1 |
| 2012/0251880 A1 | 10/2012 | Utsunomiya | |
| 2012/0295155 A1* | 11/2012 | Deng | ..................... H01B 1/122 |
| | | | 429/200 |
| 2013/0309573 A1* | 11/2013 | Ohba | ..................... H01M 4/131 |
| | | | 429/218.1 |
| 2015/0086853 A1* | 3/2015 | Matsuno | ............... H01M 4/364 |
| | | | 429/163 |

FOREIGN PATENT DOCUMENTS

| | | |
|---|---|---|
| JP | 2004-63394 A | 2/2004 |
| JP | 2009-266706 A | 11/2009 |
| JP | 2011-54324 A | 3/2011 |
| JP | 2011-228052 A | 11/2011 |
| JP | 2012-169300 A | 9/2012 |
| JP | 2012-216401 A | 11/2012 |
| JP | 2013-242997 A | 12/2013 |
| JP | 2014-96300 A | 5/2014 |

OTHER PUBLICATIONS

Feng, "Facile approach to SiOx/Si/C composite anode material from bulk SiO for lithium ion batteries", Phys.Chem. Chem. Phys., 2013, 15, pp. 14420-14426.*
Kim, "Effect of carbon types on the electrochemical properties of negative electrodesfor Li-ion capacitors", Journal of Power Sources 196 (2011) 10490-10495 (Year: 2011).*
JP-2003123740-A, Machine Translation, Mori (Year: 2003).*
International Search Report issued in Application No. PCT/JP2015/079426, dated Mar. 1, 2016 and translation thereof (7 pages).
Written Opinion of International Searching Authority issued in PCT/JP2015/079426, dated Mar. 1, 2016 (5 pages).
Written Opinion of International Searching Authority issued in PCT/JP2015/079426, dated Mar. 1, 2016 and translation thereof (11 pages).

* cited by examiner

[Fig.1]
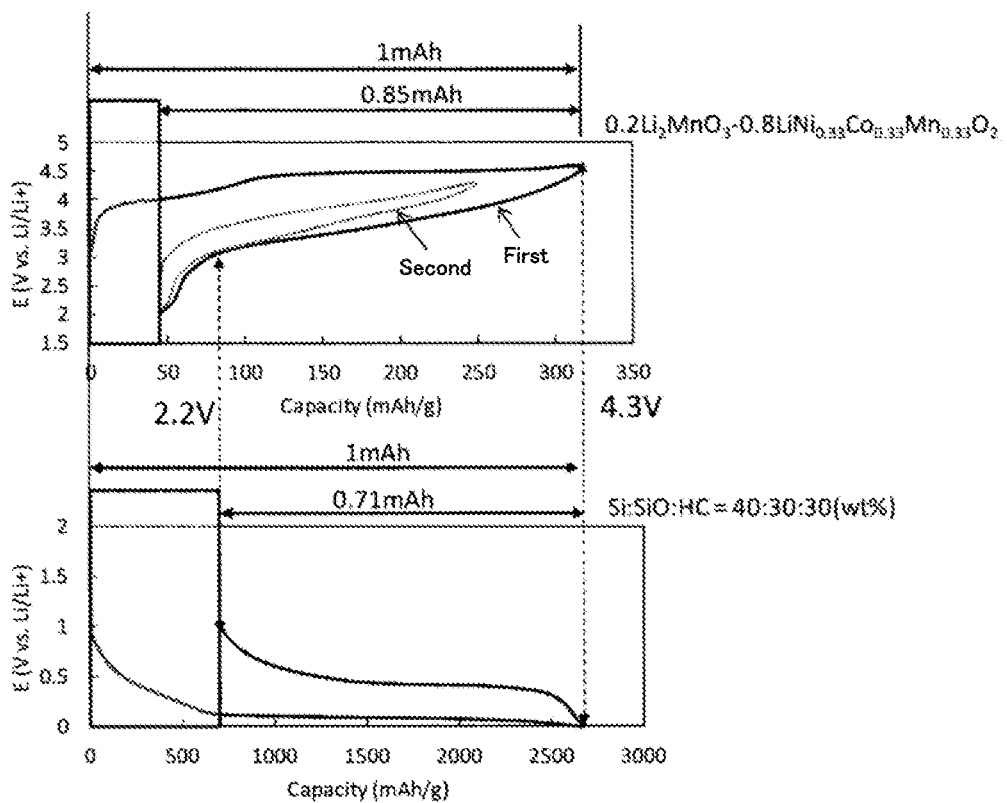
[Fig.2]
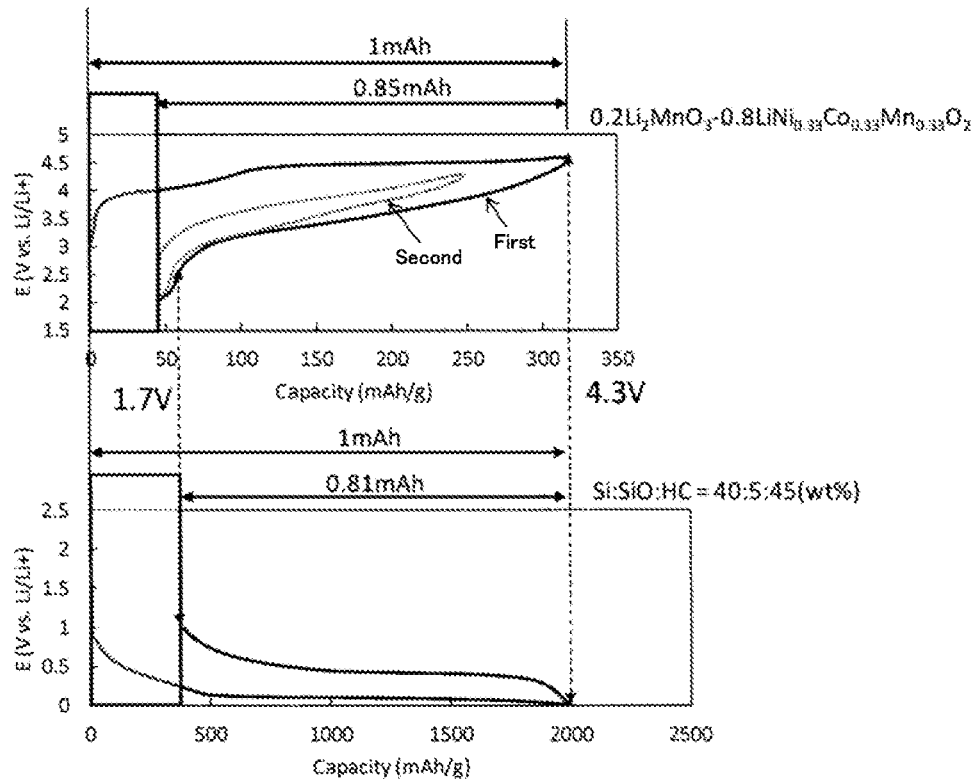

[Fig.3]
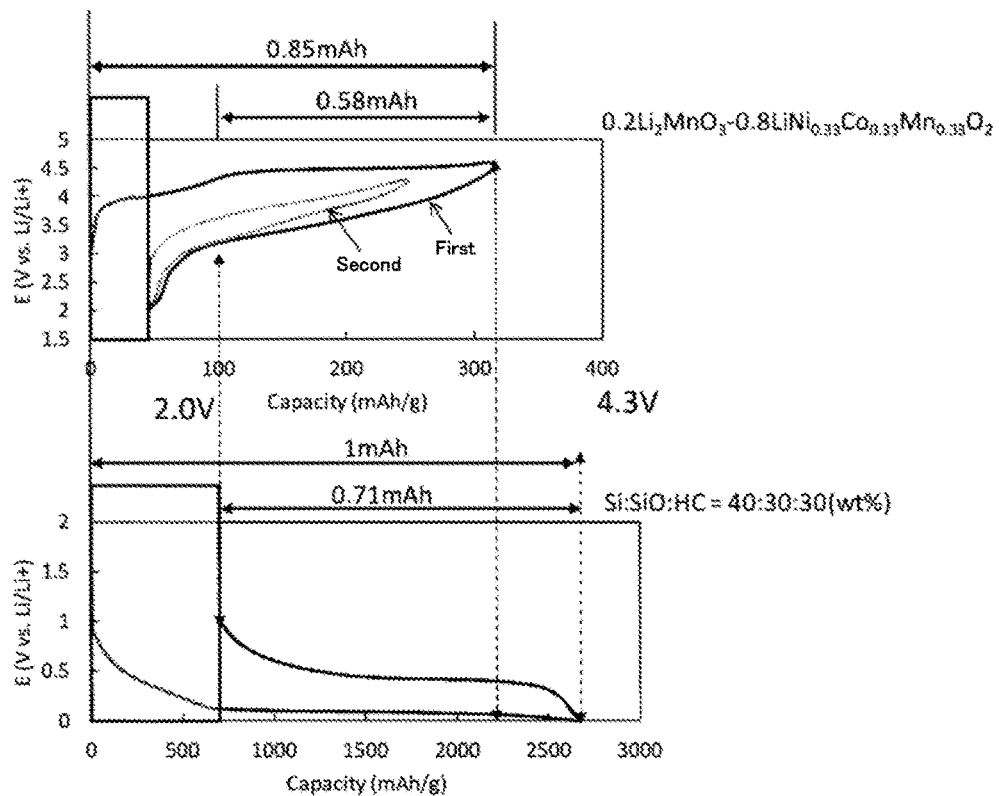
[Fig.4]
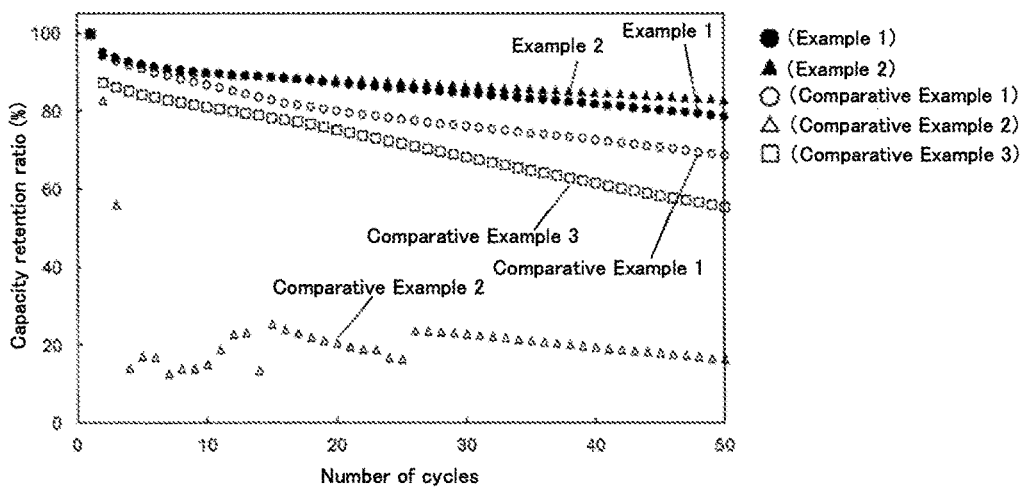

LITHIUM ION BATTERY

TECHNICAL FIELD

The present invention relates to a pre-doping free lithium ion battery having high heat resistance.

BACKGROUND ART

In recent years, developments of electric vehicles (EVs) and hybrid electric vehicles (HEVs) are aggressively pursued in the automobile industry from the viewpoint of oil substitution or a low environmental load. A lithium ion secondary battery is mainly introduced into power supplies for motor drive, and research on an increase of battery energy density is positively made for further market growth of EVs and HEVs.

In the lithium ion secondary battery, lithium cobalt oxide (LiCoO$_2$) is used as a positive electrode active material, a carbon material is used as a negative electrode active material, and a nonaqueous electrolytic solution formed by dissolving lithium ions in an organic solvent such as propylene carbonate is used as an electrolyte. These materials function as an electrode active material which reversibly absorbs and releases lithium ions by charge and discharge, and configure a so-called rocking chair type secondary battery which is electrochemically coupled with a nonaqueous electrolytic solution or a solid electrolyte.

The capacity of LiCoO$_2$ serving as a positive electrode active material depends on the amount of reversible insertion/detachment of lithium ions. That is, when an amount of Li detachment from the positive electrode active material is increased, a capacity is increased. However, when the amount of Li detachment from the positive electrode active material is increased, a crystal structure of the positive electrode is destroyed and cycle characteristics are lowered. Therefore, research on lithium-cobalt-nickel-manganese oxide in which part of Co is substituted with Li, Ni or Mn is positively made.

On the other hand, a carbonaceous material to be used as a negative electrode active material has an excellent first charge-discharge efficiency (ratio of a first discharge capacity to a first charge capacity), but since the carbonaceous material can absorb and release only 0.17 atoms of lithium per one atom of carbon, it has a problem that an increase of energy density is difficult. Specifically, a battery capacity of a hard carbon is limited to about 372 mAh/g even though a stoichiometric lithium absorption capacity can be realized.

A negative electrode active material containing Si or Sn is newly proposed as a material having a capacity density higher than that of the negative electrode active material composed of the carbonaceous material. The negative electrode active material containing Si or SiO has an advantage that a battery capacity is larger than that of the carbonaceous material.

Since the Si negative electrode active material is equal in the first charge-discharge efficiency to the carbonaceous material, it is possible to increase energy density. On the other hand, the SiO negative electrode active material has a problem that a first discharge capacity to a first charge capacity (first charge-discharge efficiency) is low. That is, in the lithium ion secondary battery in which a material containing SiO is used as a negative electrode active material, it happens that when lithium dedoped from the positive electrode at the first charge is doped into the negative electrode, part of the lithium is accumulated in the negative electrode, and does not return to the positive electrode at the subsequent discharge.

Such a lithium capacity which remains in the negative electrode after discharge and cannot be involved in the subsequent charge-discharge reaction (irreversible capacity) reduces a discharge capacity which the battery has at the first (battery capacity), and thereby, a capacity utilization factor of a positive electrode filled is lowered and energy density of a battery is lowered. Such a large irreversible capacity has become a large problem of development in the actual use in vehicle applications requiring a high capacity, and attempts to suppress the irreversible capacity are positively made.

As a technology of compensating for lithium corresponding to such an irreversible capacity, a method of previously attaching a predetermined amount of lithium powder or a lithium foil to the surface of a silicon negative electrode is proposed (refer to Patent Document 1). According to this disclosure, it is described that by preliminarily absorbing (pre-doping) lithium of an amount corresponding to a first charge and discharge capacity difference in the negative electrode, the battery capacity is increased and lowering of the cycle characteristic is further improved.

Further, in the Si or SiO negative electrode active material, since an adsorption/release amount of Li is large, changes in volume of a crystal lattice associated with charge and discharge are vigorous, and therefore there has been a problem that cycle performance is low due to deterioration of an electrode. Such a large change in volume has become a large problem of development in the actual use in vehicle applications requiring a long service life, and attempts to mitigate the changes in volume are positively made.

A battery described in Patent Document 1 can improve cycle characteristics while maintaining high energy density since lithium corresponding to an irreversible capacity is pre-doped to a negative electrode. However, since the negative electrode subjected to lithium pre-doping reacts excessively with a slight moisture, adequate consideration for safety has to be given, and therefore, such an electrode has a problem that it has to be handled in a low-humidity environment and an electrode manufacturing process becomes complicated.

Patent Document 2 describes a lithium ion secondary battery which uses a lithium transition metal composite oxide having an irreversible capacity as a positive electrode active material and a silicon-based material as a negative electrode active material. However, in the battery described in Patent Document 2, it is not described that an actual capacity of the negative electrode to an actual capacity of the positive electrode is 95% or more, and it is not considered that a first charge-discharge efficiency of the negative electrode active material is adjusted by compounding Si, SiO and HC.

Further, a conventional lithium ion secondary battery could not achieve adequate characteristics of a cycle life due to the deterioration of an electrode because the battery has a high possibility that lithium dendrite is grown on the negative electrode when charge is performed in an environment of −10° C., and a polyvinylidene fluoride (PVdF) binder swells in an environment of 45° C. or higher.

Further, for a conventional electrolytic solution for a lithium ion secondary battery, lithium hexafluorophosphate (LiPF$_6$) as a supporting electrolyte, and ethylene carbonate (EC) and ethyl methyl carbonate (EMC) as solvents have been primarily used. The reason for this is that a conductivity of a lithium ion is high, and wettability of polyolefin-based materials such as polypropylene (PP) and polyethylene (PE) with a microporous separator is relatively high because of low viscosity. However, it has been known that LiPF$_6$ is very unstable to heat and a water content and EMC is low in thermal stability. As a result, when the electrolytic solution is heated, a reaction between LiPF$_6$ and a solvent occurs. Further, LiPF$_6$ easily causes a hydrolysis reaction with water to produce hydrofluoric acid (HF). This HF exhibits corrosive nature to all substances in the battery, and it is pointed out that HF causes deterioration of a battery.

A battery does not exert good battery characteristics only by changing one component material, for example, only an active material. There may be cases where unforeseeable performance is exerted by a combination of existing materials. Therefore, in evaluation of a battery, it is necessary to evaluate even an existing substance as a battery and prove its usefulness from the result. In other words, even though a substance itself is existing, if it has not been yet evaluated as a battery, it is said to be an unknown substance in a battery material system. Moreover, since a battery which does not operate as a system is meaningless, it is necessary not only to adequately consider compatibility with active materials, a binder and an electrolytic solution, but also to consider electrodes and a battery structure.

PRIOR ART DOCUMENTS

Patent Documents

Patent Document 1: Japanese Unexamined Patent Publication No. 2011-54324
Patent Document 2: Japanese Unexamined Patent Publication No. 2011-228052

SUMMARY OF THE INVENTION

Problems to be Solved by the Invention

The present invention has been made in view of the aforementioned state of the prior art, and it is an object of the present invention to provide a lithium ion battery whose manufacturing process is simple and which has high energy density and heat resistance.

Means for Solving the Problems

The present inventors made various investigations, and consequently they found that the above-mentioned problems can be solved if a lithium ion battery is a power storage device including a negative electrode material formed by compounding Si, SiO and HC in order to adjust an initial irreversible capacity; a positive electrode active material having a first charge-discharge efficiency of 80% to 90% when charged/discharged using metal Li as a counter electrode; lithium hexafluorophosphate (LiPF$_6$) and lithium bis(oxalate) borate (LiBOB) as an electrolytic solution supporting electrolyte; and ethylene carbonate (EC) and γ-butyrolactone (GBL) as an electrolytic solution solvent, and proposes the present invention.

The present invention is a lithium ion battery capable of storing and releasing lithium ions, and being provided with a separator between a positive electrode and a negative electrode having irreversible capacity at the initial charge/discharge, and having a structure in which void portions in the separator are filled with a nonaqueous electrolytic solution including lithium ions, wherein a positive electrode active material contained in the positive electrode has a first charge-discharge efficiency of 80% to 90% when charged/discharged using metal Li as an counter electrode; a negative electrode active material contained in the negative electrode is selected from silicon compounds; in the negative electrode, lithium corresponding to the irreversible capacity at the initial charge/discharge is not doped; and the capacity ratio of the negative electrode to the positive electrode in the initial electric charge capacity of the positive electrode and the negative electrode is 0.95 or more and 1 or less.

According to the lithium ion battery of the present invention, it is possible to compensate an irreversible capacity of the negative electrode active material with an irreversible capacity of the positive electrode active material by using the above-mentioned negative electrode active material having a high capacity and the positive electrode active material having the first charge-discharge efficiency of 80-90% when charged/discharged using metal Li as an counter electrode, and thereby, it becomes possible to use a negative electrode material which is heretofore hard to be used since the irreversible capacity is large although the capacity is large. Further, the heat resistance of a battery is improved by using a binder and an electrolytic solution which are high in thermal stability. Therefore, it is possible to form a power storage device having high energy density and heat resistance and having excellent cycle characteristics.

Further, the initial irreversible capacity of the negative electrode active material can be adjusted by compounding Si, SiO and HC. Thereby, it is possible to obtain a lithium ion battery having high energy density in which the initial charge-discharge efficiency of the negative electrode material is improved. Further, the negative electrode active material preferably has a first charge-discharge efficiency of 70% or more when charged/discharged using metal Li as an counter electrode.

In the lithium ion battery of the present invention, the positive electrode active material is preferably formed of a substance represented by the following chemical formula 1:

$a$Li[Li$_{1/3}$Mn$_{2/3}$]O$_2$.(1−$a$)Li[Ni$_x$Co$_y$Mn$_z$]O$_2$ [Chemical Formula 1]

(0≤$a$≤0.3, 0≤$x$≤1, 0≤$y$≤1, 0≤$z$≤1, $x$+$y$+$z$=1)

Further, the first charge-discharge efficiency of the positive electrode is preferably 80% or more and 90% or less.

The lithium ion battery of the present invention preferably contains a CMC binder, a sodium polyacrylate binder and a sodium alginate binder in the positive electrode. Thereby, the positive electrode becomes a positive electrode capable of suppressing the swelling of the binder in a high temperature, and a power storage device having excellent heat resistance can be obtained.

In the lithium ion battery of the present invention, the negative electrode active material contains Si in an amount of 10% to 80%, SiO in an amount of 0% to 45%, and hard carbon in an amount of 0% to 80% when taking 100% by mass for a total of mass ratios of the Si, the SiO and the HC. Thereby, the initial charge-discharge efficiency of the negative electrode material is improved, and the battery becomes a power storage device having high energy density.

The lithium ion battery of the present invention preferably contains a polyimide resin in the negative electrode. Thereby, the negative electrode becomes a negative electrode capable of suppressing the swelling of the binder in a high temperature, and a power storage device having excellent heat resistance can be obtained.

In the lithium ion battery of the present invention, the electrolytic solution supporting electrolyte preferably contains at least lithium bis(oxalate) borate (LiBOB), and the electrolytic solution solvent preferably contains at least γ-butyrolactone (GBL). Thereby, the electrolytic solution becomes stable even in a high temperature, and a power storage device having excellent heat resistance can be obtained.

Effects of the Invention

According to the present invention, it is possible to provide a lithium ion battery whose manufacturing process is simple and which has high energy density and heat resistance.

BRIEF DESCRIPTION OF THE DRAWINGS

FIG. 1 shows a reversible capacity and an irreversible capacity of a positive electrode and a negative electrode of Example 1 of a lithium ion battery according to the present invention.

FIG. 2 shows a reversible capacity and an irreversible capacity of a positive electrode and a negative electrode of Example 2 of the lithium ion battery according to the present invention.

FIG. 3 shows a reversible capacity and an irreversible capacity of a positive electrode and a negative electrode of Comparative Example 1 of the lithium ion battery according to the present invention.

FIG. 4 shows cycle characteristics of the coin cells of Example 1, Example 2, Comparative Example 1, Comparative Example 2 and Comparative Example 3.

EMBODIMENTS OF THE INVENTION

Hereinafter, a lithium ion battery of an embodiment of the present invention will be described. The lithium ion battery according to the present invention is a power storage device capable of storing and releasing lithium ions, and being provided with a separator between a positive electrode and a negative electrode having irreversible capacity at the initial charge/discharge, and having a structure in which void portions in the separator are filled with a nonaqueous electrolytic solution including lithium ions, wherein a positive electrode active material contained in the positive electrode has a first charge-discharge efficiency of 80% to 90% when charged/discharged using metal Li as an counter electrode. Further, a negative electrode active material contained in the negative electrode is a mixed material of a silicon compound and a HC, and in the negative electrode, lithium corresponding to the irreversible capacity at the initial charge/discharge is not doped. With respect to a relationship of the initial electric charge capacity between the positive electrode and the negative electrode, the capacity ratio of the negative electrode to the positive electrode is 0.95 or more and 1 or less.

The negative electrode active material used in the present invention is a material obtained by compounding Si, SiO and HC. This compounded material enables to increase a capacity of the lithium ion battery of the present invention since it has high first charge-discharge efficiency and a very high capacity.

With respect to a Si or SiO negative electrode active material, since changes in volume resulting from an absorption/release reaction of lithium ions during charge and discharge, is significantly large, the negative electrode material is easily structurally deteriorated to produce cracks in an electrode in charging/discharging repeatedly. As a result of this, a reduction of a discharge capacity (cycle characteristic) after charging/discharging repeatedly has become a problem. In the present invention, by containing a HC in the negative electrode, volume expansion of a Si or SiO negative electrode active material during charge and discharge can be mitigated. Thereby, the negative electrode material can be prevented from being structurally deteriorated to produce cracks in an electrode, and a reduction of a discharge capacity (cycle characteristic) after charging/discharging repeatedly can be suppressed.

The negative electrode active material preferably contains Si in an amount of 10% to 80%, SiO in an amount of 0% to 45%, and HC in an amount of 0% to 80%, and more preferably contains Si in an amount of 40% to 80%, SiO in an amount of 0% to 10%, and HC in an amount of 10% to 60% when taking 100% by mass for a total of mass ratios of the Si, the SiO and the HC.

Further, since PVdF serving as a conventional negative electrode binder reacts with an electrolytic solution in an environment of 45° C. or higher to swell, it has had a problem that adequate characteristics of a cycle life is not achieved due to the deterioration of an electrode. In the present invention, by containing a polyimide resin in the negative electrode, swelling of the binder can be suppressed. Thereby, the negative electrode material can be prevented from being structurally deteriorated in a high temperature to produce cracks, and a reduction of a discharge capacity (cycle characteristic) after charging/discharging repeatedly can be suppressed.

The positive electrode active material used in the present invention has a first charge-discharge efficiency of 80% to 90%, preferably 85% to 90% when charged/discharged using metal Li as an counter electrode. In other words, the positive electrode active material used in the present invention has an irreversible capacity in an amount of 10% to 20%, preferably 10% to 15% with respect to a capacity of the whole active material.

Although the negative electrode active material used in the present invention has a high capacity as described above, it has a disadvantage that the first charge and discharge capacity is low and a cycle life is short. In order to solve the problem, the present inventors found that the irreversible capacity of the negative electrode active material is compensated with the irreversible capacity of the positive electrode active material by mixing a silicon compound and a HC, using the negative electrode in combination with a positive electrode having a first charge-discharge efficiency of 80% to 90% when charged/discharged using metal Li as an counter electrode, and setting a capacity ratio of the negative electrode to a positive electrode to 0.95 or more and 1 or less in the initial electric charge capacity of the positive electrode and the negative electrode when using metal Li as an counter electrode. It becomes possible to use a negative electrode material which is heretofore hard to be used since a life is short and the irreversible capacity is large although the capacity is large. In order to set the capacity ratio of the negative electrode to the positive electrode to 0.95 or more and 1 or less in the initial electric charge capacity of the positive electrode and the negative electrode when using metal Li as an counter electrode, for example, thicknesses of a film of the positive electrode active material and a film of the negative electrode active material formed at the positive electrode and the negative electrode, respectively, may be controlled.

The positive electrode active material used in the present invention is not particularly limited as long as it has a first charge-discharge efficiency of 80% to 90%, preferably 85% to 90% when charged/discharged using metal Li as an counter electrode. When the charge-discharge efficiency is less than 80%, it is not preferred since the positive electrode cannot achieve an adequate reversible capacity. When the charge-discharge efficiency is more than 90%, it is not preferred since Li of the positive electrode is trapped by an irreversible component of the negative electrode resulting in a reduction of a reversible capacity of the positive electrode. As the positive electrode active material in the present invention, a layered oxide represented by the following chemical formula 1 is suitably used.

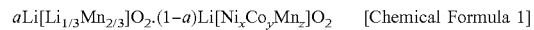
$aLi[Li_{1/3}Mn_{2/3}]O_2 \cdot (1-a)Li[Ni_xCo_yMn_z]O_2$  [Chemical Formula 1]

($0 \leq a \leq 0.3$, $0 \leq x \leq 1$, $0 \leq y \leq 1$, $0 \leq z \leq 1$, $x+y+z=1$)

Further, while as a conventional positive electrode binder, PVdF is applied, since PVdF reacts with an electrolytic solution in an environment of 45° C. or higher to swell, there has been a problem that adequate characteristics of a cycle life is not achieved due to the deterioration of an electrode. The positive electrode binder used in the present invention is a CMC binder, a sodium polyacrylate binder and a sodium alginate binder, and more preferably a sodium polyacrylate binder. Thereby, the swelling of the positive electrode can be suppressed in a high temperature to prevent the occurrence of cracks due to deterioration of an electrode structure, and a reduction of a discharge capacity (cycle characteristic) after charging/discharging repeatedly can be suppressed.

In the lithium ion battery of the present invention, the negative electrode active material preferably contains Si in an amount of 10% to 80%, SiO in an amount of 0% to 45%, and HC in an amount of 0% to 80%, and more preferably contains Si in an amount of 40% to 80%, SiO in an amount of 0% to 10%, and HC in an amount of 10% to 60% when taking 100% by mass for a total of mass ratios of the Si, the SiO and the HC. Thus, a ratio of an irreversible capacity of the negative electrode to a reversible capacity of the positive electrode can be reduced by including these Si and HC having a small irreversible capacity in the SiO negative electrode active material to form a composite (compounded). Thereby, it is possible to enhance the reversible capacity of the negative electrode material, and a power storage device which has high energy density and excellent cycle characteristics can be obtained. In addition, "to form a composite thereof" means to include the overall state in which SiO particles, Si particles and HC particles are included, and this may be a state in which particles of each are merely mixed, or may be a state in which particles of each are coupled with one another.

In the lithium ion battery of the present invention, the negative electrode active material preferably contains Si in an amount of 10% to 80%, SiO in an amount of 0% to 45%, and HC in an amount of 0% to 80%, and more preferably contains Si in an amount of 40% to 80%, SiO in an amount of 0% to 10%, and HC in an amount of 10% to 60% when taking 100% by mass for a total of mass ratios of the Si, the SiO and the HC. When the SiO content is more than 45%, it is not preferred since the ratio of the irreversible capacity of the negative electrode to the irreversible capacity of the positive electrode cannot be adequately decreased. When the HC content is more than 80%, it is not preferred since the Si content becomes small and a capacity of the negative electrode cannot be increased. By employing the above-mentioned mass ratio, the negative electrode material becomes a negative electrode material capable of mitigating the changes in volume associated with the absorption/release of lithium ions, and a lithium ion battery having a high capacity and excellent charge-discharge cycle characteristics can be obtained.

In the lithium ion battery of the present invention, the electrolytic solution supporting electrolyte preferably contains at least lithium bis(oxalate) borate (LiBOB), and the electrolytic solution solvent preferably contains at least γ-butyrolactone (GBL). Thereby, the electrolytic solution becomes stable even in a high temperature, and a power storage device having excellent heat resistance can be obtained. Further, the lithium ion battery of the present invention is more preferably configured so that the electrolytic solution supporting electrolyte contains lithium hexafluorophosphate (LiPF$_6$) and lithium bis(oxalate) borate (LiBOB), and more preferably configured so that the electrolytic solution solvent contains ethylene carbonate (EC) and γ-butyrolactone (GBL). By such a configuration, the stability of the electrolytic solution in a high temperature can be further enhanced, and a power storage device having more excellent heat resistance can be obtained.

The lithium ion battery of the present invention preferably contains lithium bis(oxalate) borate in the electrolytic solution supporting electrolyte. However, since lithium bis(oxalate) borate (LiBOB) has a low solubility in a solvent, it is preferably used in combination with LiPF$_6$. Since LiBOB is stable up to about 250° C., it is used as a material playing a role like an additive for improving the heat resistance of an electrolytic solution. However, when the electrolytic solution is used at elevated temperatures, the solubility is also improved, and therefore it becomes possible to use LiBOB as a supporting electrolyte of a high-temperature electrolytic solution. LiBOB does not have corrosive nature to an Al current collector. Moreover, since LiBOB is a halogen-free supporting electrolyte not containing fluorine, there is no fear of producing HF.

In the lithium ion battery of the present invention, ethylene carbonate (EC) and γ-butyrolactone (GBL) are preferably used in combination for a solvent of the electrolytic solution. A boiling point of ethylene carbonate (EC) is 244° C., and a boiling point of γ-butyrolactone (GBL) is 204° C. A solution obtained by mixing these materials in combination can be used as a heat-resisting electrolytic solution.

With respect to a potential range in using a solvent, EC and GBL can normally be use at around 0 to 4.5V vs. Li potential. GBL has excellent balances among permittivity, viscosity, a melting point and a boiling point and is preferred as a solvent for an electrolytic solution, but it is low in reduction resistance and oxidation resistance. The oxidation resistance of GBL itself is not high, but since it reacts in over charging to form a coating on the surface of the positive electrode, it has a function of preventing deterioration of the electrolytic solution, and thereby, it can be used even in a voltage region of 4 V range. Although GBL reacts with metal lithium since it is not high in reduction resistance, but it is possible to overcome this by combining GBL with EC.

According to the electrolytic solution for a lithium ion secondary battery of the present invention, the electrolytic solution can be used as a heat-resisting electrolytic solution since the solvent has a high boiling point and the supporting electrolyte has heat resistance.

EXAMPLES

The present invention will be described in more detail by way of examples, but the present invention is not limited to the following examples.

Example 1

(1) Preparation of Positive Electrode

A slurry-like mixture was prepared by mixing 90% by mass of Li-rich oxide (0.2Li$_2$MnO$_3$-

0.8LiNi$_{0.33}$Co$_{0.33}$Mn$_{0.33}$O$_2$, LNCMO) as a positive electrode active material, 5% by mass of sodium polyacrylate as a binder, and 5% by mass of acetylene black (AB) as a conductive material. The slurry was applied onto an aluminum foil of 20 μm in thickness serving as a current collector, dried with a drying machine at 80° C., and then made to pass between a pair of rotating rollers, and an electrode sheet was obtained using a roll press. This electrode was punched out in the form of a disk of 11 mm in diameter by an electrode punching machine, and the disk was subjected to heat treatment (under reduced pressure, at 150° C. for 24 hours) to obtain a positive electrode plate. Here, a thickness of the slurry applied onto the aluminum foil was 55 μm.

(2) Preparation of Positive Electrode Test Battery

On a lower lid of a coin cell, the positive electrode was placed with the aluminum foil side facing downward, and thereon, a separator made of a polypropylene porous membrane of 16 mm in diameter (Celgard #2400 manufactured by Hoechst Celanese Corporation) which was dried under reduced pressure at 60° C. for 8 hours and metal lithium serving as an counter electrode were laminated to prepare a positive electrode test battery. As an electrolytic solution, 1M LiPF$_6$ dissolved in a mixed solvent of ethylene carbonate (EC) and diethyl carbonate (DEC) (volume ratio of EC:DEC=1:1) was used. In addition, assembling of the positive electrode test battery was conducted in an environment of a dew-point temperature of −60° C. or lower.

In the positive electrode test battery thus prepared, that is, in a battery in which metal Li is used as an counter electrode, the first charge capacity (initial electric charge capacity) of the positive electrode was 1.00 mAh, and the first discharge capacity was 0.85 mAh. The first discharge capacity was a reversible capacity of the positive electrode. In addition, the first charge-discharge efficiency of the positive electrode was 85%.

(3) Preparation of Negative Electrode

Polyimide (PI) as a binder and AB as a conductive substance were weighed in such a way that the relative proportion of a negative electrode active material powder formed by compounding Si, SiO and HC in proportions of 40:30:30, the binder and the conductive substance is 80:2:18 (weight ratio), and these three material were dispersed in N-methylpyrrolidone (NMP), and then the resulting mixture was adequately stirred with a planetary centrifugal mixer to be formed into a slurry. The formed slurry was applied onto a high strength copper foil serving as a negative electrode current collector to prepare a negative electrode by the same method as in the positive electrode. This electrode sheet was punched out in the form of a disk of 11 mm in diameter by an electrode punching machine, and the disk was dried under reduced pressure at 350° C. for 1 hour to obtain a negative electrode plate. Here, a thickness of the slurry applied onto the high strength copper foil was 30 μm.

(4) Preparation of Negative Electrode Test Battery

As with the positive electrode, on a lower lid of a coin cell, the negative electrode was placed with a high strength copper foil side facing downward, and thereon, a separator made of a polypropylene porous membrane of 16 mm in diameter (Celgard #2400 manufactured by Hoechst Celanese Corporation) which was dried under reduced pressure at 60° C. for 8 hours and metal Li serving as an counter electrode were laminated to prepare a negative electrode test battery. As an electrolytic solution, 1M LiPF$_6$ dissolved in a mixed solvent of ethylene carbonate (EC) and diethyl carbonate (DEC) (volume ratio of EC:DEC=1:1) was used. In addition, assembling of the negative electrode test battery was conducted in an environment of a dew-point temperature of −60° C. or lower.

In a negative electrode test battery thus prepared, that is, in a battery in which metal Li is used as an counter electrode, the first charge capacity (initial electric charge capacity) of the negative electrode was 1.00 mAh, and the first discharge capacity was 0.71 mAh. Accordingly, the first charge-discharge efficiency of the negative electrode was 71% which is 70% or more.

FIG. 1 graphically shows the first charge and discharge capacity (initial electric charge capacity: mAh) of the above-mentioned positive electrode and negative electrode when using metal Li as an counter electrode. A horizontal axis shows the capacity (mAh) and a vertical axis shows a potential (V vs. Li/Li+). Since a first charge capacity (initial electric charge capacity) of the positive electrode is 1.00 mAh, and a first charge capacity (initial electric charge capacity) of the negative electrode is also 1.00 mAh, a capacity ratio of the negative electrode to the positive electrode is 1 in the initial electric charge capacity of the positive electrode and the negative electrode.

(5) Charge and Discharge Test

A battery for a charge and discharge test was prepared using the above-mentioned positive electrode, negative electrode and separator. A battery structure is a 2032 type coin cell structure in which the separator is interposed between the positive electrode and the negative electrode. As a nonaqueous electrolyte (nonaqueous electrolytic solution) contained in a void portion in the separator, 1M LiPF$_6$ and 0.05M LiBOB which were dissolved in a mixed solvent of ethylene carbonate (EC) and γ-butyrolactone (GBL) (volume ratio of EC:GBL=1:1) was used. A charge and discharge test of the 2032 type coin cell was performed at a rate of 0.1 C at 60° C. setting charge and discharge cut-off voltages to 4.6 V and 2.2 V, respectively for a first charge and discharge, and to 4.3 V and 2.2 V, respectively, for a second and subsequent charge and discharge. FIG. 4 shows a relation between a discharge capacity retention ratio (%) and number of cycles in the charge and discharge test of Example 1. In addition, a vertical axis shows a discharge capacity retention ratio (%) and a horizontal axis shows the number of cycles. The discharge capacity retention ratio is a value determined as a ratio of the discharge capacity in each cycle to the discharge capacity at the second cycle. In the charge and discharge test of Example 1, an irreversible capacity was canceled at the first cycle and a discharge capacity at the first cycle was 0.71 mAh. In addition, the discharge capacity at the second cycle of the positive electrode was 172 mAh/g. In the charge and discharge cycle test at 60° C., the discharge capacity retention ratio after 50 cycles was 80%.

Example 2

A coin cell was prepared by the same method as in Example 1 except that the negative electrode active material was prepared by compounding Si, SiO and HC in proportions of 40:5:55. A charge and discharge test of the 2032 type coin cell was performed at a rate of 0.1 C at 60° C. setting charge and discharge cut-off voltages to 4.6 V and 1.7 V, respectively, for a first charge and discharge, and to 4.3 V and 1.7 V, respectively, for a second and subsequent charge and discharge. In addition, a first charge capacity of the negative electrode was 1.00 mAh and a first discharge capacity of the negative electrode was 0.81 mAh when using metal Li as an counter electrode (Accordingly, a first charge-discharge efficiency of the negative electrode is 81% which is 70% or more). In addition, FIG. 2 graphically shows the first charge and discharge capacity (initial electric charge capacity: mAh) of the above-mentioned positive electrode and negative electrode when using metal Li as an counter electrode. Since a first charge capacity (initial electric charge capacity) of the positive electrode is 1.00 mAh, and a first charge capacity (initial electric charge capacity) of the negative electrode is also 1.00 mAh, a capacity ratio of the negative electrode to the positive electrode is 1 in the initial electric charge capacity of the positive electrode and the negative electrode. Further, FIG. 4 shows the results of the same charge and discharge test performed as in Example 1 on Example 2. In the charge and discharge test of Example 2, the discharge capacity at the second cycle of the positive electrode was 190 mAh/g. In the charge and discharge cycle test at 60° C., the discharge capacity retention ratio after 50 cycles was 83%.

Comparative Example 1

A coin cell was prepared by the same method as in Example 1. A charge and discharge test of the 2032 type coin cell was performed at a rate of 0.1 C at 60° C. setting charge and discharge cut-off voltages to 4.5 V and 2.2 V, respectively, for a first charge and discharge, and to 4.3 V and 2.3 V, respectively, for a second and subsequent charge and discharge. In addition, a first charge capacity (initial electric charge capacity) of the positive electrode was 0.85 mAh and a first discharge capacity of the positive electrode was 0.58 mAh when using metal Li as an counter electrode. FIG. 3 graphically shows the first charge and discharge capacity (initial electric charge capacity: mAh) of the above-mentioned positive electrode and negative electrode when using metal Li as an counter electrode. Further, FIG. 4 shows the results of the same charge and discharge test performed as in Example 1 on Comparative Example 1. In the charge and discharge test of Comparative Example 1, the discharge capacity at the second cycle of the positive electrode was 138 mAh/g. In the charge and discharge cycle test at 60° C., the discharge capacity retention ratio after 50 cycles was 70%.

Comparative Example 2

A coin cell was prepared by the same method as in Example 1 except that the binders of the positive electrode and the negative electrode are each a PVdF binder. A charge and discharge test of the 2032 type coin cell was performed at a rate of 0.1 C at 60° C. setting charge and discharge cut-off voltages to 4.6 V and 2.2 V, respectively, for a first charge and discharge, and to 4.3 V and 2.2 V, respectively, for a second and subsequent charge and discharge. In addition, a first charge capacity (initial electric charge capacity) of the positive electrode was 1.00 mAh and a first discharge capacity of the positive electrode was 0.70 mAh when using metal Li as an counter electrode. Further, FIG. 4 shows the results of the same charge and discharge test performed as in Example 1 on Comparative Example 2. In the charge and discharge test of Comparative Example 2, the discharge capacity at the second cycle of the positive electrode was 165 mAh/g. In the charge and discharge cycle test at 60° C., the discharge capacity retention ratio after 50 cycles was 16%.

Comparative Example 3

A coin cell was prepared by the same method as in Example 1 except that the electrolytic solution is 1M $LiPF_6$ dissolved in a mixed solvent of ethylene carbonate (EC) and γ-butyrolactone (GBL) (volume ratio of EC:GBL=1:1). A charge and discharge test of the 2032 type coin cell was performed at a rate of 0.1 C at 60° C. setting charge and discharge cut-off voltages to 4.6 V and 2.2 V, respectively, for a first charge and discharge, and to 4.3 V and 2.2 V, respectively, for a second and subsequent charge and discharge. In addition, a first charge capacity (initial electric charge capacity) of the positive electrode was 1.00 mAh and a first discharge capacity of the positive electrode was 0.71 mAh when using metal Li as an counter electrode. Further, FIG. 4 shows the results of the same charge and discharge test performed as in Example 1 on Comparative Example 3. In the charge and discharge test of Comparative Example 3, the discharge capacity at the second cycle of the positive electrode was 168 mAh/g. In the charge and discharge cycle test at 60° C., the discharge capacity retention ratio after 50 cycles was 55%.

From the results of the charge and discharge tests on Examples 1 and 2 and Comparative Examples 1 to 3, shown in FIG. 4, it is found that in Comparative Example 1 in which the capacity ratio of the negative electrode to the positive electrode is 0.85 in the first charge capacity (initial electric charge capacity) of the positive electrode and the negative electrode when using metal Li as an counter electrode, a capacity density (mAh/g) is largely lowered as the number of charge-discharge cycles is increased, and on the other hand, in Examples 1 and 2 in which the capacity ratio of the negative electrode to the positive electrode is 1 in the first charge capacity (initial electric charge capacity) of the positive electrode and the negative electrode when using metal Li as an counter electrode, a high capacity density (mAh/g) is maintained even when the number of charge-discharge cycles is increased, and the cycle characteristics are extremely good. In addition, it is thought that a boundary of the capacity ratio of the negative electrode to the positive electrode above which a reduction ratio of the capacity density (mAh/g) associated with an increase of the number of charge-discharge cycles is thought to be not so large, is present between 0.95 and 1.

Further, in the battery of Comparative Example 2 in which the binders of the positive electrode and the negative electrode are each conventional PVdF, as is apparent from the graph of FIG. 4, the capacity after 50 cycles is reduced by about 80% or more with respect to the initial capacity, and the characteristic is deteriorated in a high temperature. The reason for this is supposedly that electrode structures of the positive electrode and the negative electrode are deteriorated due to the swelling of the binder in a high temperature.

Further, in the battery of Comparative Example 3 in which the electrolytic solution is $LiPF_6$ dissolved in a mixed solvent of ethylene carbonate (EC) and γ-butyrolactone (GBL) (volume ratio of EC:GBL=1:1), as is apparent from the graph of FIG. 4, the capacity after 50 cycles is reduced by about 45% with respect to the initial capacity, and the characteristic is deteriorated in a high temperature. The reason for this is supposedly that the electrolytic solution is oxidatively decomposed at the surface of the positive electrode in a high temperature to increase internal resistance of the electrode.

As described above, the lithium ion battery of the present examples can improve the heat resistance of a battery without performing Li pre-doping and increase energy density.

INDUSTRIAL APPLICABILITY

The lithium ion battery obtained according to the present can be used for applications such as main power supplies of a mobile telecommunication devices, mobile electronic devices, electric bicycles, electric motorcycles, and electric vehicles.

The invention claimed is:

1. A lithium ion battery comprising a positive electrode, a negative electrode, a nonaqueous electrolytic solution and a separator,
wherein a positive electrode active material contained in the positive electrode has a first charge-discharge efficiency of 80% to 90% when charged/discharged using metal Li as a counter electrode;
a negative electrode active material contained in the negative electrode;
in the negative electrode, lithium corresponding to an irreversible capacity at an initial charge/discharge is not doped;
a capacity ratio of the negative electrode to the positive electrode at an initial electric charge capacity of the positive electrode and the negative electrode is 0.95 or more and 1 or less;
the negative electrode active material is a compound material consisting of pure silicon (Si), silicon monoxide (SiO) and hard carbon (HC) in a state that the pure silicon (Si), the silicon monoxide (SiO) and the hard carbon (HC) are mixed with each other, or that particles of the pure silicon (Si), the silicon monoxide (SiO) and the hard carbon (HC) are coupled with each other.

2. The lithium ion battery according to claim 1, wherein the negative electrode active material has a first charge-discharge efficiency of 70% or more when charged/discharged using metal Li as a counter electrode.

3. The lithium ion battery according to claim 1, wherein the negative electrode active material contains Si in an amount of 10% to 80%, SiO in an amount equal to or less than 45%, and HC in an amount equal to or less than 80% when taking 100% by mass for a total of mass ratios of the Si, the SiO and the HC.

4. The lithium ion battery according to claim 1, wherein the negative electrode contains a polyimide resin.

5. The lithium ion battery according to claim 1, wherein the positive electrode active material is represented by the following chemical formula 1:

$$a\text{Li}[\text{Li}_{1/3}\text{Mn}_{2/3}]\text{O}_2 \cdot (1-a)\text{Li}[\text{Ni}_x\text{Co}_y\text{Mn}_z]\text{O}_2 \quad \text{[Chemical Formula 1]}$$

in which $0 \leq a \leq 0.3$, $0 \leq x \leq 1$, $0 \leq y \leq 1$, $0 \leq z \leq 1$, and $x+y+z=1$.

6. The lithium ion battery according to claim 1, wherein the positive electrode contains at least one or more selected from the group consisting of carboxy methyl cellulose (CMC), sodium polyacrylate and a sodium alginate binders.

7. The lithium ion battery according to claim 1, wherein the nonaqueous electrolytic solution includes a solvent and a supporting electrolyte, the solvent contains at least γ-butyrolactone (GBL), and the supporting electrolyte contains at least lithium bis(oxalate) borate (LiBOB).

* * * * *